United States Patent
Johanning (10) Patent No.: US 10,568,547 B1
(45) Date of Patent: Feb. 25, 2020

(54) MULTIFUNCTIONAL ASSESSMENT SYSTEM FOR ASSESSING MUSCLE STRENGTH, MOBILITY, AND FRAILTY

(71) Applicant: The Board of Regents of the University of Nebraska, Lincoln, NE (US)

(72) Inventor: Jason M. Johanning, Omaha, NE (US)

(73) Assignee: The Board of Regents of the University of Nebraska, Lincoln, NE (US)

( * ) Notice: Subject to any disclaimer, the term of this patent is extended or adjusted under 35 U.S.C. 154(b) by 139 days.

(21) Appl. No.: 15/289,664

(22) Filed: Oct. 10, 2016

Related U.S. Application Data (60) Provisional application No. 62/238,807, filed on Oct. 8, 2015.

(51) Int. Cl.
*A61B 5/11* (2006.01)
*A61B 5/00* (2006.01)
*A61B 5/22* (2006.01)

(52) U.S. Cl.
CPC .......... *A61B 5/1116* (2013.01); *A61B 5/0077* (2013.01); *A61B 5/112* (2013.01); *A61B 5/1121* (2013.01); *A61B 5/1125* (2013.01); *A61B 5/1128* (2013.01); *A61B 5/224* (2013.01); *A61B 5/225* (2013.01); *A61B 5/6891* (2013.01); *A61B 5/1115* (2013.01); *A61B 5/6894* (2013.01)

(58) Field of Classification Search
CPC ... A61B 5/1115; A61B 5/1116; A61B 5/1121; A61B 5/1125; A61B 5/1128; A61B 5/224; A61B 5/225; A61B 5/6891; A61B 5/6894; A61B 5/742; A61B 5/7445
See application file for complete search history.

(56) References Cited

U.S. PATENT DOCUMENTS

| 5,570,301 A | * | 10/1996 | Barrus | A61B 5/103 |
| | | | | 702/150 |
| 8,211,014 B2 | * | 7/2012 | David | A61B 5/7278 |
| | | | | 128/897 |
| 2002/0044059 A1 | * | 4/2002 | Reeder | A61B 5/0002 |
| | | | | 340/573.1 |

(Continued)

OTHER PUBLICATIONS

Cooper, Zara, MD, MSc et al., "Comparison of Frailty Measures as Predictors of Outcomes After Orthopedic Surgery" The American Geriatrics Society, JAGS 64:2464-2471, 2016.

(Continued)

*Primary Examiner* — Devin B Henson
(74) *Attorney, Agent, or Firm* — Suiter Swantz pc llo (57) ABSTRACT

This disclosure describes a multifunctional assessment system that can include a seating platform (e.g., chair, bench, or the like) for a subject, an image-capturing device, and one or more sensors directly or indirectly coupled to the seating platform. The image-capturing device (e.g., camera or motion sensor) records ambulatory motion of the subject, and the one or more sensors can detect at least one of a force or a motion of the subject, such as a seating motion, posture, weight distribution, and motions or forces associated with the subjects overall health. For example, motions or forces detected can be associated with a subject's ability to get up off the seating platform, sit upright, grip strength, and so forth.

16 Claims, 2 Drawing Sheets

(56) References Cited

U.S. PATENT DOCUMENTS

| | | | | |
|---|---|---|---|---|
| 2004/0186358 | A1* | 9/2004 | Chernow | A61B 5/0002 600/300 |
| 2007/0136102 | A1* | 6/2007 | Rodgers | A61B 5/1113 705/3 |
| 2015/0038881 | A1* | 2/2015 | Gokhale | A61B 5/1116 600/595 |
| 2015/0061873 | A1* | 3/2015 | Hyde | A61B 5/6894 340/573.1 |
| 2015/0196209 | A1* | 7/2015 | Morris | A61B 5/02141 600/480 |

OTHER PUBLICATIONS

Fritz, Stacy L., MSPT, PhD et al., "Measuring Walking Speed Clinical Feasibility and Reliability", Topics in Geriatric Rehabilitation, vol. 28, No. 2, 91-96, Apr.-Jun. 2012.

Leong, Darryl P. et al., "Prognostic value of grip strength: findings from the Prospective Urban Rural Epidemiology (PURE) study", Lancet 2015, vol. 386, 266-273, Jul. 18, 2015.

Lusardi, Michelle M., PT, DPT, PhD., "Is Walking Speed a Vital Sign? Absolutely", Topics in Geriatric Rehabilitation, vol. 28, No. 2, 67-76, Apr.-Jun. 2012.

Sayer, Avan Aihie et al., "Grip strength and mortality: a biomarker of ageing?", Lancet, vol. 386, 226-227, Jul. 18, 2015.

Schiller, Ben, "You Can Tell How Long Someone Is Going to Live by the Strength of Their Grip", https://www.fastcoexist.com/3046503/you-can-tell-how-long-someone-is-going-to-live-by-the-strength-of-their-grip, 1-4, May 27, 2015.

Sprint, Gina et al., "Towards Automating Clinical Assessments: A Survey of the Timed Up and Go (TUG)", School of Electrical Engineering and Computer Science, Washington State University, Pullman, WA, St. Luke's Rehabilitation Institute, Spokane, WA, 1-42.

* cited by examiner

MULTIFUNCTIONAL ASSESSMENT SYSTEM FOR ASSESSING MUSCLE STRENGTH, MOBILITY, AND FRAILTY

BACKGROUND

Assessments of muscle strength, mobility, and frailty are utilized in the medical field for diagnostic and prognostic purposes. These assessments can be utilized in a variety of medical disciplines including geriatric medicine, oncologic medicine, sports medicine, physical and rehabilitative therapy, and diagnostic medicine. These assessments can be used to predict future events such as mortality, morbidity, or functional decline.

SUMMARY

A multifunctional assessment system is disclosed. In implementations, the multifunctional assessment system can include a seating platform (e.g., chair, bench, or the like) for a subject, an image-capturing device, and one or more sensors directly or indirectly coupled to the seating platform. The image-capturing device (e.g., camera or motion sensor) records ambulatory motion of the subject, and the one or more sensors can detect at least one of a force or a motion of the subject, such as a seating motion, posture, weight distribution, and motions or forces associated with the subjects overall health. For example, motions or forces detected can be associated with a subject's ability to get up off the seating platform, sit upright, grip strength, and so forth.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter

DRAWINGS

The detailed description is described with reference to the accompanying figures. The use of the same reference numbers in different instances in the description and the figures may indicate similar or identical items.

DETAILED DESCRIPTION

Overview

Several assessment tools exist to assess muscle strength and mobility in the medical field. These assessment tools can be used for both diagnostic and prognostic purposes. These assessments can also be utilized in assessing frailty. Some of the most widely used assessments include grip strength, walking speed, and timed up and go.

A grip strength test measures the maximum isometric strength of the hand and forearm muscles. Grip strength is a known predictor of all-cause mortality, cardiovascular mortality, incident cardiovascular disease, myocardial infarction, and stroke. Grip strength can be used to diagnose diseases, to evaluate and compare treatments, to document progression of muscle strength, and to provide pre and postoperative feedback or feedback during the rehabilitation process as a measure indicating the level of hand function. Handgrip strength can be measured by the amount of static force in pounds that the hand can squeeze around a handgrip dynamometer. These results can be compared to known normative average values for both men and women.

The walking speed test is a known performance measure used to assess walking speed over a short distance. Walking speed is an indicator that can be used to determine functional mobility, gait and vestibular function; can be predictive of future events such as mortality and functional decline; is a predictor of outcomes of rehabilitation; and can reflect underlying neuromotor physiological processes. Walking speed can also be an indicator of overall comorbid burden of illness. Walking speed is measured in meters per second as the subject (patient) walks around a walking path. The subject's speed is measured over the middle portion of the path, allowing a portion of the path to account for acceleration and deceleration. The ideal length of the walking path is 20 meters, with walking speed recorded over the middle 10 meters. Many clinical and research settings employ walking speed tests of different lengths, but recent research exists examining the accuracy of shorter distances and strongly supports a 4 meter walk as adequate. Measured walking speed can be compared against normative age and gender data. Those walking at speeds less than 6 m/s are most vulnerable to adverse health events and early mortality. Walking speed can currently be measured by a stopwatch with visual estimation of starting and stopping points, automatic timers, or pressure-activated walkways (e.g., GAITRite systems, CIR systems, etc.). Walking speed has strong clinometric characteristics and many researchers consider it to be a vital sign.

Measurements of other temporal and spatial elements of gait (e.g., stride and step length, stride symmetry, single and double-limb support, and step width) can be indicative of falls and frailty in the elderly. These measures can provide a more in-depth analysis of health status than measuring walking speed alone. Gait characteristics can be measured by standardized visual assessment tools (e.g., Tinetti Test, Dynamic Gait Index, Functional Gait Assessment, etc.), electromyography, floor-to-floor reaction forces, 2-demensional versus 3-dimensional motion analysis, or body-worn kinematic sensors. The validity of these measurement tools differs depending on age and disease state of the subject.

The timed up and go (TUG) test is a known assessment of basic mobility skills. The TUG test is a measurement of the time in seconds for a person to rise from sitting from a standard arm chair, walk 3 meters at a normal pace, turn, walk back to the chair, and sit down. This duration is indicative of a subject's ambulatory abilities, balance, and possibly risk of falling. The test has been used in many patient populations, including the elderly, arthritis patients, stroke patients, vertigo patients, and Parkinson's disease patients. There are many methods of administering the TUG test including a timed visual test, video-conferencing, Kinect sensors, wearable sensors (e.g. inertial measurement units, iTUG, surface electromyography, accelerators, magnetometers, etc.), mobile device sensors (e.g. smartphone sensors, etc.), and ambient sensors (e.g., aTUG, etc.). Testing methods incorporating technology provide a more thorough assessment, as these devices are capable of capturing elements in addition to TUG duration (e.g., maximum angular velocity during sit-to-stand and stand-to-sit, component duration, maximum trunk angle change, joint angles, average step time, maximum step time, number of steps, cadence, etc.), and help compensate for movement strategies employed by subjects. Wearable sensors and mobile device sensors also allow for in-home assessment by the subjects themselves. While TUG is an important and beneficial standardized test, its limitations include low test-retest reliability due to differences in the chair used, differences in the subject's footwear, the use of assistive devices (e.g., walker, cane, etc.), and medication changes.

Additionally, a combination of the above assessments can be used to perform multifaceted assessment. Such an assessment can be used to assess for multidimensional disease states, such as frailty. Frailty is a multidimensional geriatric syndrome characterized by increased vulnerability to stressors as a result of reduced capacity of different physiological systems. It has been associated with an increased risk of adverse health-related outcomes in older persons, including falls, disability, hospitalizations morbidity, mortality, and has further been associated with biological abnormalities (e.g., biomarkers of inflammation). The occurrence of frailty increases incrementally with advancing age, is more common in older women than men, and is more common among those of lower socio-economic status. Frail older adults are at high risk for major adverse health outcomes, including disability, falls, institutionalization, hospitalization, and mortality. Frailty can also be indicative of underlying pathogenesis. Frailty is highly predictive of poor surgical outcomes including death, disability and institutionalization. Associations between specific disease states are associated with frailty, including cardiovascular disease, diabetes mellitus, renal insufficiency and other diseases in which inflammation is prominent.

Frailty can be assessed in a variety of ways. The most commonly used assessment used primarily in the research setting is the frailty phenotype (Fried assessment), which is defined by the presence of three of five symptoms including poor muscle strength, slow gait speed, unintentional weight loss, exhaustion, and sedentary behavior. Validated frailty assessment tools include the Cardiovascular Health Study frailty screening measure, the FRAIL questionnaire screening tool, the Clinical Frailty Scale, and the Gérontôpole Frailty Screening Tool. Monitoring the subject's vital signs (e.g., temperature, heart rate, blood pressure, etc.) may also be necessary. A comprehensive geriatric assessment may be necessary to adequately assess frailty. An accurate assessment of frailty allows for the implementation of interventions (e.g., nutrition changes, exercise plans) that can lead to reduced hospital stays and health care costs.

Despite the known efficacy of a variety of assessment tools for muscle strength, mobility, and frailty, the utilization of these assessment tools in practice is limited by feasibility. Performing a comprehensive body of assessments currently requires time, physical space, and multiple pieces of medical equipment. A lack of knowledge in interpreting assessment tools may also be a barrier to utilization of assessments. Walking speed tests, in particular, can require a significant amount of space (e.g., 20 meter walkway ideally) to administer, and automatic timers or pressure-activated electronic walkways necessary to enhance accuracy can be costly. Further, developing a complete assessment of a subject's health status with currently available assessment tools often requires repeated testing of the subject, or multiple practitioners administering the test. For example, it would be difficult for one practitioner to both visually assess walking speed and other characteristics of gait simultaneously. Additionally, automated assessments provide enhanced accuracy because they permit continuous and calibrated measurements. However, there is a lack of automated assessment tools that can measure multiple variables simultaneously.

This disclosure describes a multifunctional assessment system that can include a seating platform (e.g., chair, bench, or the like) for a subject, an image-capturing device, and one or more sensors directly or indirectly coupled to the seating platform. The image-capturing device (e.g., camera or motion sensor) records ambulatory motion of the subject, and the one or more sensors can detect at least one of a force or a motion of the subject, such as a seating motion, posture, height, weight distribution, and motions or forces associated with the subject's overall health. For example, motions or forces detected can be associated with the subject's ability to get up off the seating platform, sit upright, grip strength, and so forth. In some implementations, the multifunctional assessment system can further include a second computing device in communication from with the first computing device. The second computing device can be configured to receive input from the subject.

In implementations, the multifunctional assessment system is configured to generate and analyze data based on the subject's exercises and input based on normative values. The first computing device is configured to generate reports or instructions, allowing for a complete subject assessment to be performed. The first computing device can be configured to communicate the reports or instructions to the second computing device.

Example Implementations

Figure 1:
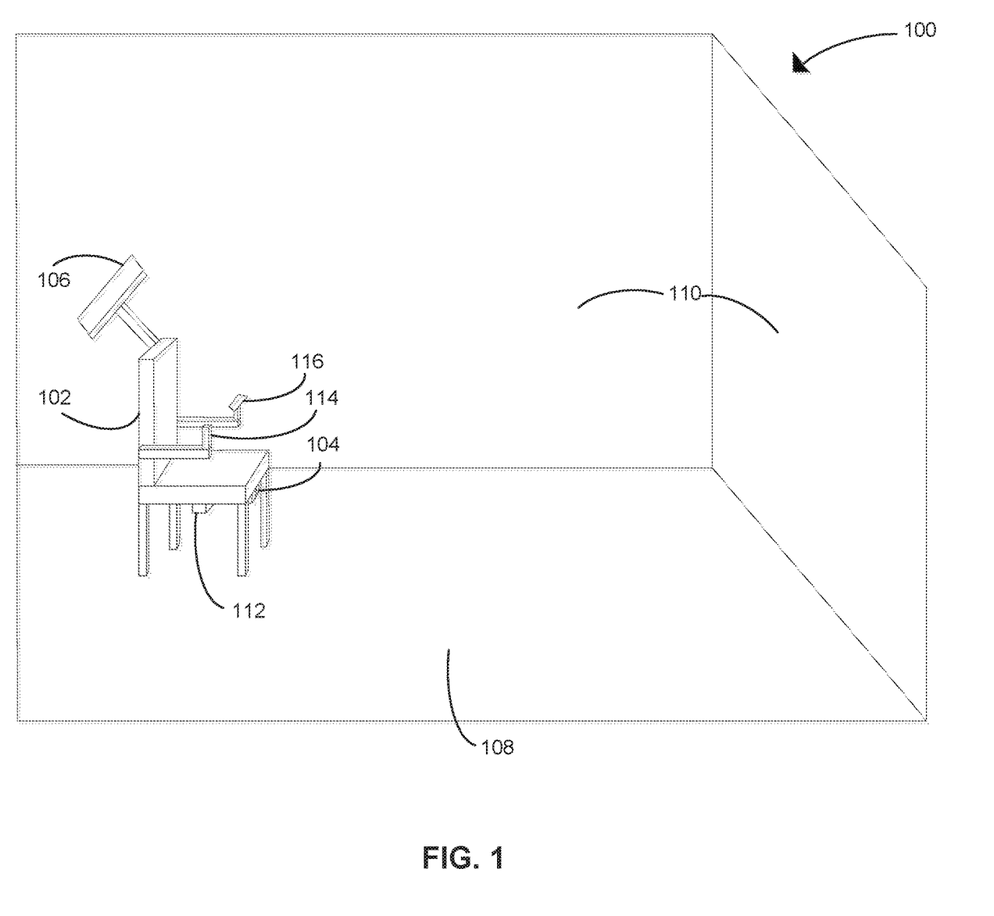
FIG. 1 illustrates an environment in an example implementation that is operable to facilitate the multifunctional assessment system in accordance with the present disclosure.

FIG. 1 illustrates a multifunctional assessment system 100 in accordance with an embodiment of the present disclosure. In one or more implementations, the multifunctional assessment system 100 is modular and/or tubular that can communicatively communicate with one or more computing devices (as described in greater detail below) allowing a patient to self-report one or more patient medical characteristics. This functionality also allows for medical support entry. The multifunctional assessment system 100 includes a seating platform 102 (e.g., chair, bench, and the like). The multifunctional assessment system 100 further includes one or more image capture devices (e.g., one or more cameras 104). The cameras 104 are communicatively coupled to a first computing device 106. In a preferred embodiment, the cameras 104 and the first computing device 106 are affixed to the seating platform 102. However, this embodiment is provided by way of example only and is not meant to be restrictive of the present disclosure. In other embodiments, at least one of the cameras 104 or the first computing device 106 can be freestanding (e.g., cameras placed in other areas of the room). In another embodiment, at least one of the cameras 104 may be affixed to the first computing device 106.

The cameras 104 are configured to capture images and per-pixel depth information in a field-of-view (FOV) of the cameras 104. Thus, the cameras 104 may function as depth sensing devices. In some embodiments, the cameras 104 may be depth cameras, such as Red-Green-Blue depth (RGB-D) cameras operable to capture depth frame image data representing one or more depth frame images and to capture color frame image data representing one or more color (RGB) frame images. Cameras 104 can also include, but are not limited to: a near infrared light configured to generate a near infrared light pattern onto the objects within the FOV, a complementary-metal-oxide-semiconductor (CMOS) sensor device configured to measure the depth of each object within the FOV, or a CMOS camera device. In implementations, RGB-D cameras can identify various objects within the FOV of the cameras 104 and estimate the depth of the identified objects through various depth approximation techniques. For example, the RGB-D cameras may transmit a structured light pattern in the near-infrared spectrum and utilize suitable parallax techniques to estimate the depth of the objects within the cameras' 104 FOV in order to generate depth image data representing one or more depth frame images. Thus, the cameras 104 capture data to allow for generation of a depth frame image representing at least partially objects within the cameras' 104 FOV. The cameras 104 can also capture color frame image data representing a color frame image at least partially representing objects within the cameras' 104 FOV. It is noted that "cameras 104" can include any camera that is capable of obtaining distance or depth information in addition to two-dimensional pixel information. Those skilled in the art will also appreciate that although the plural tense, "cameras," is often used herein, cameras 104 can comprise a single camera or sensor array without departing from the scope of this disclosure.

In an implementation, the cameras 104 provide the ability to capture and map three-dimensional video imagery in addition to two-dimensional video imagery. For example, the cameras 104 can capture two-dimensional data for a plurality of pixels that comprise the video image. These data values represent color values for the pixels (e.g., red, green, and blue [RGB] values for each pixel that represents the environment). Thus, objects captured by the cameras 104 can appear as two-dimensional objects via a monitor (e.g., a display, as described in greater detail herein). As mentioned above, the cameras 102 can also capture depth data within the cameras' 104 FOV. Thus, the cameras 104 are configured to capture the x and y components (e.g., x and y values) of the environment within the FOV using RGB values (captured image data, such as the color frame data representing a color frame image) for each pixel in the scene. However, the cameras 104 are configured to also capture the z-components of the environment, which represent the depth values (e.g., depth estimate data corresponding to the z-axis) within the environment. In this regard, the camera(s) 104 provide the ability to capture and map (e.g., with the processor described below) the third-dimension in addition to two-dimensional video imagery. The camera(s) 104 capture two-dimensional data for a plurality of pixels that comprise the video image. These values are color values (e.g., color frame image data) for the pixels (e.g., the RGB values for each pixel). In addition, the camera(s) 104 also capture the z-components of the scene (e.g., depth frame image data), which represent the depth values for the scene.

In some implementations, the cameras 104 can capture images representing environmental views within the FOV of the cameras 104. For example, in a specific implementation, the cameras 104 may capture image data representing a floor 108 and a walls 110 within the FOV. In other implementations, the cameras 104 may be utilized to track a subject's mobility progress.

The multifunctional assessment system 100 can also include one or more ambient sensors 112 (e.g., pressure sensor, force sensor, motion sensor, temperature sensor, infrared motion sensor, blood pressure cuff, heart rate detector, etc.), which may be affixed to the seating platform 102. For example, the one or more ambient sensors 112 can include one or more bodily force sensors positioned on the seating platform or affixed to support points that hold the seating platform (e.g., chair legs). In some implementations, the one or more bodily force sensors can be used to detect a patient's weight. The patient's height and/or other bodily dimensions can be determined using a scale or measuring stick extending from the seating platform, or in some embodiments, the cameras 104 can be used to determine a patient's height or other dimensions (e.g., based upon a known distance to the patient or a comparison between the patient and one or more objects having predetermined dimensions). The ambient sensors 112 can be affixed to one or more locations on the seating platform 102 (e.g., legs, seat, backrest, etc.). The ambient sensors 112 can be communicatively coupled to the first computing device 106. The ambient sensors 112 can be utilized to collect data about the subject's ambulatory mobility.

The multifunctional system 100 can also include one or more sensors configured to detect grip strength (e.g., handgrip dynamometers 114, etc.). The handgrip dynamometers 114 can be affixed to one or both arms of the seating platform 102. The handgrip dynamometers 114 can be communicatively coupled to the first computing device 106. The handgrip dynamometers 114 can be utilized to collect grip strength data from the subject. In some embodiments, a patient's body weight, height, other bodily dimensions, and user-entered information (e.g., age) can be used to determine the patient's BMI. The combination of BMI and grip strength with other patient information (e.g., age, gender, etc.) can provide a useful metric of patient health, frailty, and so forth. In one or more implementations, the handgrip dynamometers 114 can be detachable with respect to the multifunctional system 100.

In some implementations, the multifunctional assessment device can include a second computing device 116. The second computing device 116 can be communicatively coupled to the first computing device 106. The second computing device 116 can be configured to receive input from the patient. In other embodiments, the first computing device 106 is accessible to the patient and the health care professional. Accordingly, the first computing device 106 may perform operations described herein with regards to the second computing device 116 (i.e., both systems integrated into the first computing device 106). For example, the first computing device 106 can be attached to a holder that can swivel or rotate between at least two positions, a first viewing/input position for the patient and second viewing/input position for the healthcare provider. In other embodiments, the first computing device 106 can be a mobile device (e.g., tablet, smartphone, notebook, etc.) that is in wireless communication with the various sensors described above. In such cases, the first computing device 106 may be handled between the patient and the healthcare professional.

Figure 2:
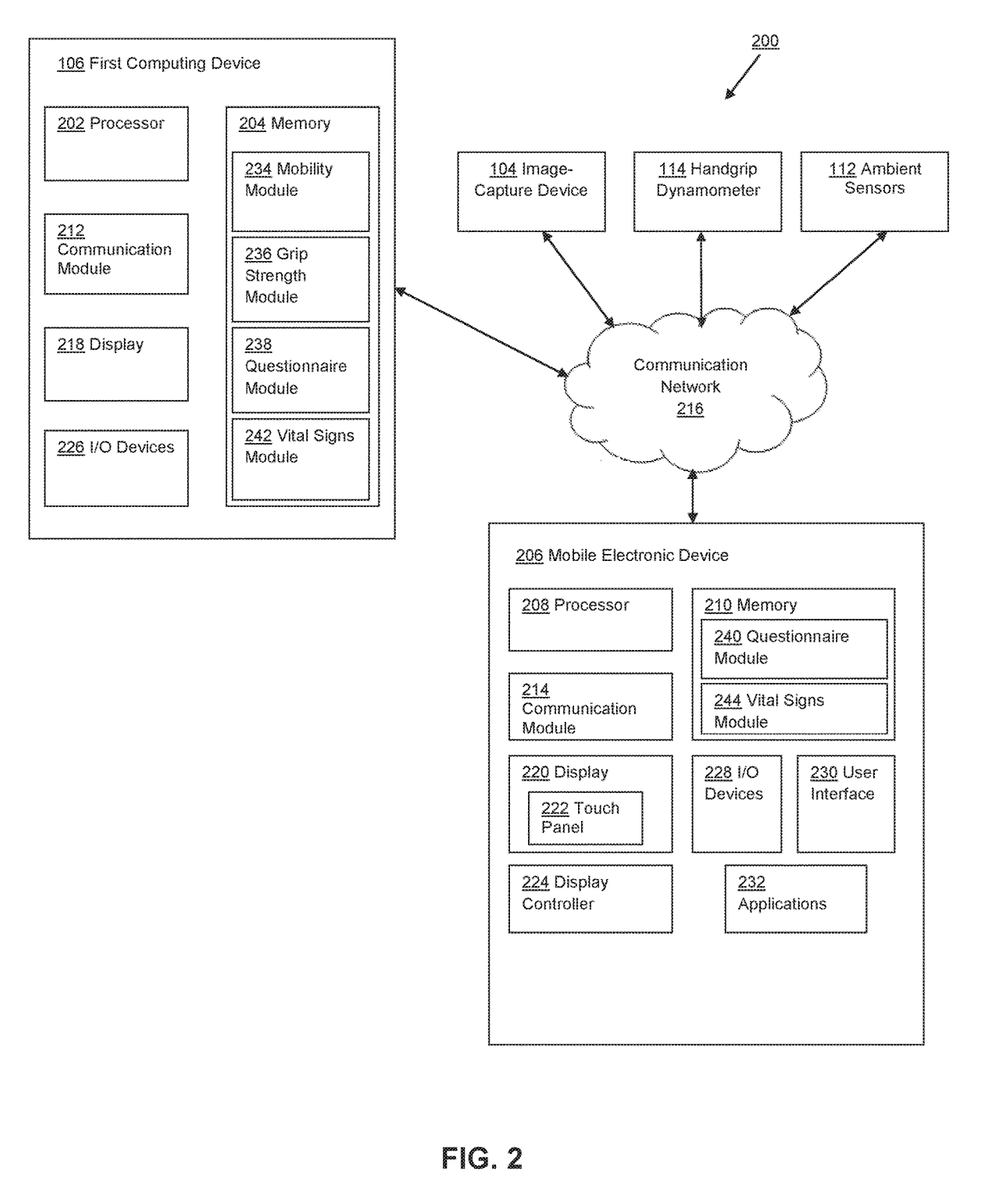
FIG. 2 is a block diagram of a multifunctional assessment system in accordance with the present disclosure.

FIG. 2 illustrates an environment 200 in an example implementation that is operable to facilitate the multifunctional assessment system in accordance with the present disclosure. The cameras 104 furnish the captured data (color frame image data, depth frame image data) to the first computing device 106. At least one of the ambient sensors 112 or the handgrip dynamometer 114 furnish data to the first computing device 106. The first computing device 106 can include any one of a variety of processing devices. For example, the first computing device 106 may be a server computing device, a desktop computing device, a laptop computing device, a mobile computing device, or the like. As shown in FIG. 1, the first computing device 106 includes a processor 202 and a memory 204. The camera(s) 104 provides data representing the video images to the processor 202. The processor 202 utilizes this data along with other sensor inputs or user/patient inputs to generate various test results or information regarding the patient.

In some implementations, the multifunctional assessment device can include a second computing device 116. The second computing device 116, such as a mobile electronic device 206 (e.g., notebook, tablet, smartphone, or the like) or any other computing device configured to receive user inputs (e.g., desktop computer). The second computing device 116 is capable of communicating with the first computer device 106 directly (e.g., via wired connection) or over a wireless network. In implementations, the second computing device includes a mobile electronic device 206 as shown in FIG. 2, where the mobile electronic device 206 includes a processor 208 and a memory 210.

In FIG. 2, the first computing device 106 and the mobile electronic device 206 are illustrated as each including a respective processor 202 or 208; a respective memory 204 or 210; and a respective communication module 212 or 214. In the following discussion, elements of the first computing device 106 are described with reference to FIG. 2. Respective elements and/or reference numbers related to the mobile electronic device 206 are shown in parentheses. Where appropriate, elements of the first computing device 106 and mobile electronic device 206 are described separately.

The processor 202 (208) provides processing functionality for the first computing device 106 (mobile electronic device 206) and may include any number of processors, micro-controllers, or other processing systems and resident or external memory for storing data and other information accessed or generated by the computing device 106 (mobile electronic device 206). The processor 202 (208) may execute one or more software programs (e.g., modules) that implement techniques described herein. For example, the processor 202, in conjunction with one or more modules as described herein, is configured to generate a depth mask (i.e., video image) of the environment based upon the depth estimate data (e.g., z-component data) captured by the cameras 104. For example, one or more modules are configured to cause the processor 202 to continually monitor the depth value of at least substantially all of the pixels that represent the captured environment and stores the greatest (deepest) depth value associated with each pixel. For instance, the modules cause the processor 202 to continually monitor for a pre-determined amount of time (e.g., a plurality of frames) the depth value of the pixels and stores the deepest depth value measured during the time interval. Thus, the depth mask comprises an accumulation of depth values and each value represents the deepest depth value of a pixel measured over the time interval. The processor 202 can then be instructed to generate a point cloud based upon the depth mask that includes a set of point values that represent the captured environment.

The memory 204 (210) is an example of tangible computer-readable media that provides storage functionality to store various data associated with the operation of the first computing device 106 (mobile computing device 206), such as the software program (e.g., a non-transitory computer-readable medium embodying a program executable by the processor 202 (208)) and code segments mentioned herein, or other data to instruct the processor 202 (208) and other elements of the first computing device 106 (mobile computing device 206) to perform the operations described herein.

The first computing device 106 is communicatively coupled to the mobile electronic device 206 a communication network 216 through a communication module 212 (214) included in the first computing device 106 (mobile electronic device 206). The first computing device 106 is also communicatively coupled to at least one of the cameras 104, ambient sensors 112, or handgrip dynamometer 114 over the communication network 216 through the communication module 212. The communication module 212 (214) may be representative of a variety of communication components and functionality, including, but not limited to: one or more antennas; a browser; a transmitter and/or receiver; a wireless radio; data ports; software interfaces and drivers; networking interfaces; data processing components; and so forth.

The communication network 216 may comprise a variety of different types of networks and connections that are contemplated, including, but not limited to: the Internet; an intranet; a satellite network; a cellular network; a mobile data network; wired and/or wireless connections; and so forth. Examples of wireless networks include, but are not limited to: networks configured for communications according to: one or more standard of the Institute of Electrical and Electronics Engineers (IEEE), such as 802.11 or 802.16 (Wi-Max) standards; Wi-Fi standards promulgated by the Wi-Fi Alliance; Bluetooth standards promulgated by the Bluetooth Special Interest Group; Near Field Communication (NFC); and so on. Wired communications are also contemplated such as through universal serial bus (USB), Ethernet, serial connections, and the like.

The first computing device 106 is also communicatively coupled to a display 218 to display information to a user of the computing device 104. In embodiments, the display 218 can include a LED (light emitting diode) display, a LCD (Liquid Crystal Diode) display, a TFT (Thin Film Transistor) LCD display, a LEP (Light Emitting Polymer), PLED (Polymer Light Emitting Diode) display, or the like, configured to display text and/or graphical information such as a graphical user interface. The processor 202 is configured to request depth image data and color frame image data from the cameras 104 (e.g., image capture device) and create an association between the depth image data and the color frame image data. In an implementation, the processor 202 can provide the associated data to the display 218 for display purposes. For example, the processor 202 may be configured to cause the display of video imagery that represents the captured environment at the display 218. The processor 202 can also request data from at least one of the ambient sensors 112 or handgrip dynamometer 114 (e.g., applied force, etc.). The processor 202 can also provide the associated data to the display 218 for display purposes.

As shown in FIG. 1, the mobile electronic device 206 includes a touch-sensitive display 220, which can be implemented using a liquid crystal display, an organic light emitting diode display, or the like. In some embodiments, the touch-sensitive display 220 may include a touch panel 222. The touch panel 222 may be, but is not limited to: a capacitive touch panel, a resistive touch panel, an infrared touch panel, combinations thereof, and the like. Thus, the display 220 may be configured to receive input from a user and display information to the user of the mobile electronic device 206. For example, the display 220 displays visual output to the user. The visual output may include graphics, text, icons, video, interactive fields configured to receive input from a user, and any combination thereof (collectively termed "graphics"). In some embodiments, some or all of the visual output may correspond to user-interface objects, further details of which are described below.

The display 220 is communicatively coupled to a display controller 224 that is configured to receive and/or transmit electrical signals to the touch-sensitive display 220. In an implementation, the touch panel 222 includes a sensor, an array of sensors, or the like, configured to accept input from a user based upon haptic and/or tactile contact. The touch panel 222, in combination with the display controller 224 (along with any associated modules and/or sets of computer-readable instructions in memory 210), detects a point of contact (or points of contact), as well as any movement or breaking of the contact, on the touch panel 222 and converts the detected contact (e.g., a finger of the user, a stylus, etc.) into electrical signals representing interactions with user-interface objects (e.g., buttons, custom views, icons, web pages, images, web page links, etc.) that are displayed through the display 220.

The computing device 106 (mobile electronic device 206) may further include one or more input/output (I/O) devices 226 (228; e.g., a keypad, buttons, a wireless input device, a thumbwheel input device, a track stick input device, and so on). The I/O devices 226 (228) may include one or more audio I/O devices, such as a microphone, speakers, and so on. Thus, I/O devices 226 (228) may include a keyboard configured to receive user input. In an implementation, the keyboard may be integrated with the computing device 106 (mobile electronic device 206), or the keyboard may be a peripheral device that is configured to interface with the device 106 (206) (e.g., via a USB port, etc.)

The mobile electronic device 206 is illustrated as including a user interface 230, which is storable in memory 210 and executable by the processor 208. The user interface 230 is representative of functionality to control the display of information and data to the user of the mobile electronic device 206 via the display 220. In some implementations, the display 220 may not be integrated into the mobile electronic device 206 and may instead be connected externally using universal serial bus (USB), Ethernet, serial connections, and so forth. The user interface 230 may provide functionality to allow the user to interact with one or more applications 232 of the mobile electronic device 206 by providing inputs via the touch panel 222 and/or the I/O devices 228. For example, the user interface 230 may cause an application programming interface (API) to be generated to furnish functionality to an application 232 to configure the application for display by the display 220 or in combination with another display. In embodiments, the API may further furnish functionality to configure the application 232 to allow the user to interact with an application by providing inputs via the touch panel 222 and/or the I/O devices 228.

Applications 232 may comprise software, which is storable in memory 210 and executable by the processor 208, to perform a specific operation or group of operations to furnish specified functionality to the mobile electronic device 206. Example applications may include content resource management applications, cellular telephone applications, instant messaging applications, email applications, address book applications, and so forth.

Example Mobility Tracker Implementation

In one or more implementations the multifunctional assessment system 100 may be utilized to track a subject's mobility. For example, the cameras 104 may be affixed to the chair 102. The subject's regimen may include one or more mobility exercises (e.g., TUG test, extended TUG test, walking speed test, etc.). Thus, the multifunctional assessment system 100 may be utilized to track the subject's progress. As shown in FIG. 2, the first computing device 106 includes a mobility module 234 that is storable in memory 204 and executable by the processor 202.

The mobility module 234 is configured to cause the processor 202 to generate a depth mask (image) representing the environment 100. Based upon the depth mask, the module 234 is configured to cause the processor 106 to generate a point cloud representing the environment 100. Once the point cloud representing the environment 100 has been identified, the processor 202 identifies one or more object points (pixels) within the field of view (FOV) of the cameras 104.

The module 234 is configured to cause the processor 202 to detect and monitor the subject's mobility exercise (e.g., TUG, extended-TUG, walking speed etc.) occurring with the FOV of the cameras 104. Thus, different assessments can be implemented to fit the needs of the subject and environmental constraints (e.g., limited space, limited time, etc.). In some one implementations the module 234 is configured to cause the processor 202 to identify one or more characteristics about the subject's mobility (e.g., ambulatory speed, velocity, distance, step length, number of turn steps, etc.). In some implementations, the module 234 is configured to cause the processor 202 to identify one or more characteristics about the subject's movement during the mobility exercise (e.g., joint angles, step height, etc.). Indentifying multiple characteristics about the subject's mobility allows for a more complete assessment of the subject. In another implementation, the module 234 is configured to cause the processor 202 to identify an assistive device, such as a walker, that the subject may be utilizing in the subject's exercise. In other implementations, the module 234 can be used to identify characteristics about the subject's body (e.g., type of footwear, corrective eyewear, etc.). Thus, factors that may cause variance and hinder test-retest reliability in mobility assessments can be identified and accounted for.

The module 234 can be configured to cause the processor 202 to segment the potential body (e.g., feet) points to isolate one or more body (e.g., feet 514) segments (e.g., a plurality of pixels representing the feet). The processor 202 is configured to determine three dimensional tracked points (e.g., track the movement of each foot) based upon the feet segments. In an implementation, the module 234 causes the processor 202 to take the mean-shifted center of a subset of points in each identified foot segment that are higher (higher y-component) as compared to the mean shifted center of the remaining subset of points in the foot segment. The module 234 is configured to cause the processor 202 to store the location of each tracked point in the memory 204. The processor 202 is configured to create a weighted distance between the current tracked points and the stored track points that have a greater change in the horizontal directions as compared to the vertical direction. Thus, the processor 202 measures or tracks the movement of the feet based upon collected data associated with the identified feet segments.

A weighted coefficient may then be determined based upon one or more suitable distribution methods. For example, the processor 202 may utilize a Gaussian distribution of weighted distances to determine a weighted coefficient that decays via a Gaussian distribution over time. Time may be defined as the difference between the time stamps of the current tracked points and the time stamps of the previously tracked points (e.g., tracked points associated with previous frames that are stored in the memory 204). The tracked points may then be passed through one or more parsing algorithms. The processor 202 may then output the weighted sum value of the current tracked points and previously tracked points using this weighted coefficient. The weighted sum value is utilized to reduce jitter associated with the tracked objects. The values may be utilized to monitor the subject's mobility exercise. For example, one or more values may be utilized to generate one or more graphs, values, instructions, reports, or the like, associated with the mobility exercise. Thus, the subject's therapist, doctor, or the like, can monitor the subject's mobility. For example, the processor 202 may be configured to generate an at least near real-time interactive report allowing the practitioner and/or subject to view data and/or results associated with the exercise. In another example, the processor 202 may be configured to generate an at least near real-time instruction based upon the exercise. The instruction may include pre-programmed instructions for improving the exercise performed, additional exercises the subject may find of interest, and so forth. The instructions and/or reports may be presented via the display 218, or the like. In some implementations, the processor 202 can be configured to communicate the instructions and/or results to the mobile electronic device 206. The instructions and/or reports may be presented via the display 220, or the like. It is contemplated that the subject may perform varying types of mobility exercises that can be tracked utilizing the system 100.

In implementations, ambient sensors 112 can be affixed to the seating platform 102, as described above. The module 234 can be configured to cause the processor 202 to collect force or motion data from the ambient sensors. In an example embodiment, force sensors can be affixed to the seating platform 102 to determine the subject's weight distribution on the seating platform 102. In another example embodiment, one or more infrared light sensors can be affixed to the seating platform 102 to detect posture of the subject (e.g., whether the subject's back has made contact with the backrest of the seating platform 102, and the like). The processor 202 can incorporate this data with the algorithm-generated data described above to generate one or more graphs, values, instructions, reports, or the like, associated with the mobility exercise. The processor 202 may generate an at least near real-time interactive report allowing the practitioner and/or subject to view data and/or results associated with the exercise. In another example, the processor 202 may generate an at least near real-time instruction based upon the exercise. The instruction may include pre-programmed instructions for improving the exercise performed, additional exercises the subject may find of interest, and so forth. The instructions and/or reports may be presented via the display 218, or the like. In some implementations, the processor 202 can communicate the instructions and/or results to the mobile electronic device 206. The instructions and/or reports may be presented via the display 220, or the like.

Example Grip Strength Tracker Implementation

In implementations, one or more handgrip dynamometers 114 can be affixed to the seating platform 102 as described above. Each handgrip dynamometer 114 can be configured to measure the amount of static force in pounds that the hand can squeeze around the handgrip dynamometer 114. As shown in FIG. 2, the computing device 106 includes a grip strength module 236 that is storable in memory 204 and executable by the processor 202. The grip strength module 236 is configured to cause the processor 106 to collect data from the handgrip dynamometers 114. In an example implementation, the processor 202 can be configured to compare grip strength data to normative values. In another example implementation, the processor 202 can be configured to track the subject's grip strength over time. The processor 202 can be configured to incorporate grip strength data with part or all of the data generated from the mobility module 234, described above to generate one or more graphs, values, instructions, reports, or the like. In another example, the processor 202 may be configured to generate an at least near real-time interactive report allowing the practitioner and/or subject to view data and/or results associated with the exercise. In another example, the processor 202 may be configured to generate an at least near real-time instruction based upon the exercise. The instruction may include pre-programmed instructions for improving the exercise performed, additional exercises the subject may find of interest, and so forth. The instructions and/or reports may be presented via the display 218, or the like. In some implementations, the processor 202 can be configured to communicate the instructions and/or results to the mobile electronic device 206. The instructions and/or reports may be presented via the display 220, or the like.

Example Subject Input Implementation

In one or more implementations the multifunctional assessment system 100 may be used to analyze data inputted by the subject. The subject's regimen may include one or more questionnaire assessments (e.g., cognitive assessments, social questions, nutritional questions, health status questions, medication questions, etc.). As seen in FIG. 2, the computing device 106 (mobile computing device 206) includes a questionnaire module 130 (140) that is storable in memory 204 (210) and executable by the processor 202 (208). The questionnaire module 238 can be configured to cause the processor 202 to communicate a series of questions selected from a database to the questionnaire module of the mobile electronic device (206). The questionnaire module 240 of the mobile electronic device 206 can be configured to cause the processer 208 to display the pre-selected questions to the subject on the visual display 220. The display 220 can be configured to receive the subject's responses to the questions via the touch panel 222. The communication module 214 can be configured to communicate the subject's responses to the first computing device 106.

The processor 202 can incorporate the subject input generated by the questionnaire module 238 with part or all of the data generated from the mobility module 234 and the grip strength module 236, described above, to generate one or more graphs, values, instructions, reports, or the like. In another example, the processor 202 may generate a real-time or near real-time interactive report allowing the practitioner and/or subject to view data and/or results associated with the exercise. In another example, the processor 202 may generate a real-time or near real-time instruction or additional questions based upon the subject input and/or the results/data associated with the exercise. The instruction may include pre-programmed instructions for additional assessments, additional exercises the subject may find of interest, and so forth. The instructions and/or reports may be presented via the display 218, or the like. In some implementations, the processor 202 can be configured to communicate the instructions, additional questions, and/or results to the mobile electronic device 206. The instructions and/or reports may be presented via the display 220, or the like.

Example Vital Signs Implementation

In one or more implementations the multifunctional assessment system 100 may be used to measure vital signs for the subject (e.g., temperature, heart rate, blood pressure, etc.). As seen in FIG. 2, the computing device 106 (mobile computing device 206) includes a vital signs module 242 (244) that is storable in memory 204 (210) and executable by the processor 202 (208). The vital signs module 242 can be configured to cause the processor 202 to communicate with the mobile electronic device (206) to run one or more application 232 contained on the mobile electron device (206). The application(s) 232 can be configured to measure one or more vital signs (e.g., temperature, heart rate, blood pressure, etc.) of the subject. The vital signs module 244 of the mobile electronic device 206 can be configured to cause the processer (208) collect vital signs data the application(s) 232. However, this method of collecting vital signs data is provided by way of example only and is not meant to be restrictive of the present disclosure. In other implementations, the vital signs module 242 (244) can be configured to cause the processor 202 (208) to receive vital signs input from the practitioner or subject respectively, or from pre-existing data (e.g., on a server, etc.). The communication module 214 of the mobile electronic device 206 can be configured to communicate the vital signs data collected to the first computing device 106.

The processor 202 can incorporate the subject input generated by the vital signs module 242 with part or all of the data generated from one or more of the mobility module 234, grip strength module 238, or questionnaire module 242 described above, to generate one or more graphs, values, instructions, reports, or the like. In another example, the processor 202 may generate an at least near real-time instruction based upon the subject input. The instruction may include pre-programmed instructions for improving vital signs, dietary recommendations, additional exercises the subject may find of interest, and so forth. The instructions and/or reports may be presented via the display 218, or the like. In some implementations, the processor 202 can be configured to communicate the instructions and/or results to the mobile electronic device 206. The instructions and/or reports may be presented via the display 220, or the like.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A multifunctional assessment system comprising:
a seating platform for a subject;
an image-capturing device coupled to the seating platform and configured to record timed up and go (TUG) of the subject from the seating platform and further configured to record ambulatory motion of the subject when the subject is at a distance from the seating platform;
one or more infrared light sensors coupled to the seating platform, the one or more infrared light sensors configured to detect a posture of the subject by detecting whether a back of the subject is in contact with a backrest of the seating platform;
one or more sensors coupled to the seating platform, the one or more sensors configured to detect at least one of a force or a motion of the subject, the one or more sensors including a grip strength detecting device configured to detect a grip force applied by the subject; and
a computing device in communication with the image-capturing device and the one or more sensors, the computing device including:
a memory configured to store one or more modules; and
a processor coupled to the memory, the processor being configured to execute the one or more modules to cause the processor to:
receive data associated with the recorded TUG and ambulatory motion of the subject from the image-capturing device and data associated with the at least one of the force or the motion of the subject from the one or more sensors; and
determine at least one health measurement for the subject based upon the data representing the recorded TUG and ambulatory motion of the subject and the data representing the at least one of the force or the motion of the subject.

2. The multifunctional assessment system of claim 1, wherein the one or more modules, when executed by the processor, are configured to cause the processor to determine an ambulatory speed of the subject based upon the data received from the image-capturing device.

3. The multifunctional assessment system of claim 1, further comprising a secondary computing device including a processor and a memory.

4. The multifunctional assessment system of claim 3, wherein the secondary computing device is in communication with the computing device.

5. The multifunctional assessment system of claim 3, wherein the secondary computing device is configured to receive input from the subject.

6. The multifunctional assessment system of claim 3, wherein the secondary computing device is configured to provide an instruction for the subject.

7. The multifunctional assessment system of claim 1, wherein the one or more sensors further include a force sensor configured to detect a bodily force applied by the subject.

8. The multifunctional assessment system of claim 1, wherein the image-capturing device is coupled to a lower surface of the seating platform.

9. A multifunctional assessment system comprising:
a seating platform for a subject;
an image-capturing device coupled to the seating platform and configured to record timed up and go (TUG) of the subject from the seating platform and further configured to record ambulatory motion of the subject when the subject is at a distance from the seating platform;
one or more infrared light sensors coupled to the seating platform, the one or more infrared light sensors configured to detect a posture of the subject by detecting whether a back of the subject is in contact with a backrest of the seating platform;
one or more sensors coupled to the seating platform, the one or more sensors configured to detect at least one of a force or a motion of the subject, the one or more sensors including a grip strength detecting device configured to detect a grip force applied by the subject; and
a computing device affixed to the seating platform by a holder configured to swivel or rotate between at least two positions including at least a first position for use by the subject and a second position for use by a healthcare provider, the computing device in communication with the image-capturing device and the one or more sensors, the computing device including:
a memory configured to store one or more modules; and
a processor coupled to the memory, the processor being configured to execute the one or more modules to cause the processor to:

receive data associated with the recorded TUG and ambulatory motion of the subject from the image-capturing device and data associated with the at least one of the force or the motion of the subject from the one or more sensors; and determine at least one health measurement for the subject based upon the data representing the recorded TUG and ambulatory motion of the subject and the data representing the at least one of the force or the motion of the subject.

10. The multifunctional assessment system of claim 9, wherein the one or more modules, when executed by the processor, are configured to cause the processor to determine an ambulatory speed of the subject based upon the data received from the image-capturing device.

11. The multifunctional assessment system of claim 9, further comprising a secondary computing device including a processor and a memory.

12. The multifunctional assessment system of claim 11, wherein the secondary computing device is in communication with the computing device.

13. The multifunctional assessment system of claim 11, wherein the secondary computing device is configured to receive input from the subject.

14. The multifunctional assessment system of claim 11, wherein the secondary computing device is configured to provide an instruction for the subject.

15. The multifunctional assessment system of claim 9, wherein the one or more sensors further include a force sensor configured to detect a bodily force applied by the subject.

16. A multifunctional assessment system comprising:
a seating platform for a subject;
an image-capturing device coupled to the seating platform and configured to record timed up and go (TUG) of the subject from the seating platform and further configured to record ambulatory motion of the subject when the subject is at a distance from the seating platform;
one or more infrared light sensors coupled to the seating platform, the one or more infrared light sensors configured to detect a posture of the subject by detecting whether a back of the subject is in contact with a backrest of the seating platform;
a detachable grip strength detecting device configured to detect a grip force applied by the subject;
one or more sensors coupled to the seating platform, the one or more sensors configured to detect at least one of a force or a motion of the subject;
a computing device affixed to the seating platform and positioned for use by a healthcare provider, the computing device in communication with the image-capturing device and the one or more sensors, the computing device including:
a memory configured to store one or more modules; and
a processor coupled to the memory, the processor being configured to execute the one or more modules to cause the processor to:
receive data representing the recorded TUG and ambulatory motion of the subject from the image-capturing device, data representing the at least one of the force or the motion of the subject from the one or more sensors, and data representing the grip force; and determine at least one health measurement for the subject based upon the data representing the recorded TUG and ambulatory motion of the subject, the data representing the at least one of the force or the motion of the subject, and the data representing the grip force; and
a second computing device affixed to the seating platform and positioned for use by the subject, the second computing device in communication with the computing device, the second computing device configured to receive input from the subject.

* * * * *